US008654336B2

(12) United States Patent
Levy

(10) Patent No.: US 8,654,336 B2
(45) Date of Patent: Feb. 18, 2014

(54) OPTICAL MEASURING DEVICE

(75) Inventor: Nathan A Levy, Ra'anana (IL)

(73) Assignee: Hewlett-Packard Indigo B.V., Maastricht (NL)

( * ) Notice: Subject to any disclaimer, the term of this patent is extended or adjusted under 35 U.S.C. 154(b) by 55 days.

(21) Appl. No.: 13/410,698

(22) Filed: Mar. 2, 2012

(65) Prior Publication Data

US 2013/0229659 A1 Sep. 5, 2013

(51) Int. Cl.
*G01N 21/00* (2006.01)
(52) U.S. Cl.
USPC .................................................. 356/440
(58) Field of Classification Search
USPC .................................................. 356/440
See application file for complete search history.

(56) References Cited

U.S. PATENT DOCUMENTS

| 5,683,118 | A | | 11/1997 | Slocum |
| 5,726,751 | A | * | 3/1998 | Altendorf et al. ............. 356/246 |
| 5,915,678 | A | | 6/1999 | Slocum et al. |
| 6,193,430 | B1 | | 2/2001 | Culpepper et al. |
| 2011/0083505 | A1 | | 4/2011 | Allen, IV et al. |
| 2011/0154645 | A1 | | 6/2011 | Morgan |
| 2011/0240849 | A1 | | 10/2011 | Wright |
| 2011/0240850 | A1 | | 10/2011 | Wright et al. |

FOREIGN PATENT DOCUMENTS

| WO | WO 00/62971 | 10/2000 |
| WO | WO 2010/148333 A2 | 12/2010 |

OTHER PUBLICATIONS

Culpepper; "Design of Quasi-Kinematic Couplings"; Precision Engineering 28, 2004; pp. 338-357.
Culpepper et al.; Quasi-Kinematic Couplings for Low-Cost Precision Alignment of High-Volume Assemblies; Transactions of the ASME, vol. 126, May, 2004; pp. 456-463.
Anastasios et al.; "Kinematic Coupling Interchangeability"; Precision Engineering 28, 2004; pp. 1-15.
"Folkers and Rojas"; downloaded on Dec. 20, 2011 from website:. http://web.mit.edu/~folkersr/www/academia/precision.html; downloaded.

* cited by examiner

Primary Examiner — Tu Nguyen

(57) ABSTRACT

A device, system and method to measure an optical characteristic of a fluid, the device including a plurality of components consecutively arranged and coupled together via quasi kinematic or kinematic coupling. The consecutively arranged components define a void within the device. The void encloses a measuring set-up for measuring at least one optical characteristic of a fluid passing through a gap. The gap is located at an intersection between an optical path of the measuring set-up and a flow path of the fluid.

18 Claims, 4 Drawing Sheets

OPTICAL MEASURING DEVICE

BACKGROUND

Densitometers can measure the passage of light through a transparent or semitransparent material. The measured density of a measurable substance is typically determined by measuring attenuation in the intensity of light which reaches the optical detector of the densitometer after passing through the measurable substance, the measurement being related to the absorption of light of the measurable substance.

Most densitometers include a light source, often a laser, aimed at a photoelectric cell, arranged with a gap in between so as to allow placing the measurable substance in the gap. The electric current that is generated by the photovoltaic cell of the densitometer is typically directly proportional to the intensity of the incident light, and thus the optical density of the measurable substance is determined by comparing the generated current with a reference current value that corresponds to the passing of light from the light source to the photovoltaic cell when the gap is kept empty.

A multi-component device may be considered kinematically constrained when each of the degrees of freedom is fully constrained and typically, none are over-constrained.

Kinematic couplings or joints may typically refer to machined mechanical contacts. In some examples, the kinematic couplings may involve a kinematic tooth configured to be inserted into a kinematic slot.

Quasi-kinematic constraints typically allows for a small amount of over-constraint while providing high precision. Quasi-kinematic coupling typically includes contacts between corresponding machined mechanical contacts. In some examples, these contacts may be a cylinder on a flat surface or a ball in a cone. Typically, in contrast to kinematic coupling, by reducing the surface contact to a line, over-constraint may, in some examples, be reduced from three degrees of freedom to two degrees. Since line contacts typically only weakly over-constrain an interface between to mechanical contacts, more deterministic relationships may be able to be formed. These more deterministic relationships may provide improved repeatability in the construction of a mechanical unit or device.

BRIEF DESCRIPTION OF THE DRAWINGS

Examples are described in the following detailed description and illustrated in the accompanying drawings in which.

Figure 1:
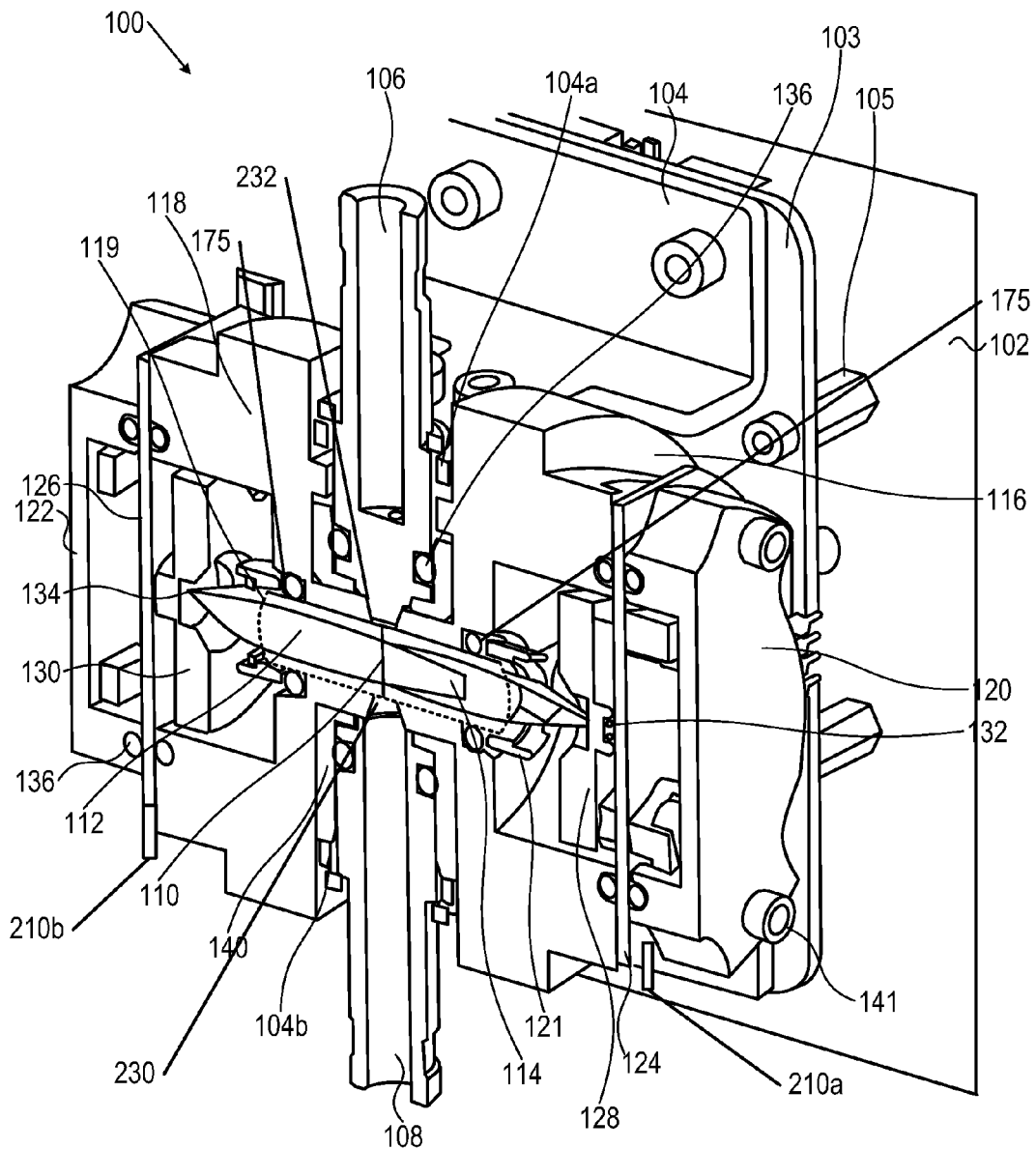
FIG. 1 is a schematic illustration of a horizontal, longitudinal cross-section according to an example.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the methods and apparatus. However, it will be understood by those skilled in the art that the present methods and apparatus may be practiced without these specific details. In other instances, well-known methods, procedures, and components have not been described in detail so as not to obscure the present methods and apparatus.

Although the examples disclosed and discussed herein are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method examples described herein are not constrained to a particular order or sequence. Additionally, some of the described method examples or elements thereof can occur or be performed at the same point in time.

Unless specifically stated otherwise, as apparent from the following discussions, it is appreciated that throughout the specification, discussions utilizing terms such as "adding", "associating" "selecting," "evaluating," "processing," "computing," "calculating," "determining," "designating," "allocating" or the like, refer to the actions and/or processes of a computer, computer processor or computing system, or similar electronic computing device, that manipulate, execute and/or transform data represented as physical, such as electronic, quantities within the computing system's registers and/or memories into other data similarly represented as physical quantities within the computing system's memories, registers or other such information storage, transmission or display devices.

FIG. 1 is a schematic illustration of a horizontal, longitudinal cross-section between a front and a back of a densitometer, along the long axis, and through frontal plane of the densitometer, the construction of the densitometer employing quasi-kinematic design elements.

An optical measuring device, typically a densitometer 100 may be manufactured as a multi-component measuring device. The device may typically be made up of at least two components, the components arranged consecutively, e.g., in a straight line.

The device typically has a high tolerance to within a few microns, typically +/−10 microns.

Densitometer may be constructed from materials, including combinations of materials, polymers and alloys. Densitometer 100 typically has a base plate 102, the base plate configured to support the separate components of the device.

In some examples, densitometer 100 may be configured to determine the percentage of solids in a fluid. In some examples, densitometer 100 may be configured to determine the amount of solid particles within a fluid. In some examples densitometer may be configured to determine the percentage of non-volatile substances (% NVS) in the fluid, such as, for example, % NVS, where the NVS are pigments of a colorant of ink for a printer via measuring light absorbance of the ink as it passes through densitometer 100.

Base plate 102 may include numerous niches, grooves, and/or additional structures for use in the construction of device 100, or in the integration of device 100 within in a larger device.

In some examples, this larger device may be a printer.

In some examples, densitometer 100 may be waterproof, or watertight. In some examples, densitometer 100 may be configured to be immersed in a liquid, e.g., ink. In some examples, densitometer 100 may be configured to be part of a larger assembly, e.g., a pathway for ink from an ink reservoir to a printer head.

A support plate 103 is typically coupled to base plate 102. In some examples, support plate 103 may be coupled to base plate 102 via a support column 105. In some examples, there may be one or a plurality of support columns 105 coupling support plate 103 to base plate 102. In some examples, spacer support columns 105 may be configured to provide a predetermined space between base plate 102 and support plate 103. In some examples, spacer support columns 105 may be configured to couple support plate 103 to base plate 102 without necessarily adding space between support plate 103 and base plate 102. In some examples, spacer support columns may be configured to house screws to couple separate components of densitometer 100.

Support structures 104a and 104b may be typically coupled to support plate 103. Support structure 104a typically may be coupled to an upper portion of densitometer 100, near an inlet 106. Support structure 104b may be coupled to a lower portion of densitometer 100, near an outlet 108.

Typically, inlet 106 may provide for a passage of a fluid from outside densitometer 100, in some examples, from an ink reservoir. In some examples, inlet 106 may provide for a passage of fluid through gap 110 within densitomter 100, and out densitometer 100 via outlet 108. Outlet 108 may lead to a printer head.

In some examples, once fluid has passed through a gap 110, the gap may be rinsed, the rinsing solution passing into gap 110 via rinse channels, including an upper rinse channel 232 and a lower rinse channel 230.

Gap 110 may be configured to provide travel of a fluid past focusing lens 112 and collimating lens 114. Gap 110 may, in some examples, may have a width. Typically the width may be between 250 and 400 microns wide, e.g., 300 microns wide.

Typically, focusing lens 112 and collimating lens 114 may be configured to focus a signal, e.g., light from a light source 132, e.g., a laser or an emitter, or other light sources, through gap 110. The emitted light may be collimated via collimating lens 114, prior to the light being detected by a receiver 134, e.g., a photodiode or other sensor or detector. In some examples, lens 112 and 114 may be rod lenses.

In some examples, densitometer may have a measuring set-up for measuring at least one optical characteristic of a fluid passing through gap 110. Typically measuring set-up may include optical sight source 132, lens 112, lens 114 and receiver 134. Typically, the optical characteristic being measured may include the optical density of the fluid.

Gap 110 is typically positioned at the intersection between the light from light source 132—the light typically travelling on an optical pathway through lens 112, gap 110, lens 114 and a receiver 134, and the flow of fluid from inlet 106 through gap 110 and through outlet 108.

In some examples, the flow of fluid may be perpendicular to the optical pathway. In some examples, the flow of fluid may be nearly perpendicular to the optical pathway. In some examples, the flow of fluid bisects gap 110 through the middle of gap 110. In some examples, the flow of fluid might not bisect gap 110 through the middle of gap 110.

In some examples, light source 132 may include a laser with a power of between 65 mw to 85 mW, e.g., 70 mW. For example, light source may include a 780 nm 70 mW laser. Other lasers may also be used.

In some examples, densitometer 100 may be configured to measure a dynamic range of signals, e.g., light from a laser, typically a range of 90 decibel milliwatts (dBm).

Typically, the signals may include measurable and/or determinable characteristics and/or properties. These include the frequency of the signal, the shape of signal and the amplitude of signal. In some examples, the signal may be describable as a wave function. In some examples, the signal may be describable as a sinusoid, i.e., a mathematical function describing a smooth, and in some examples, repetitive oscillation. Other characteristics and/or properties of signals may also be measurable and/or determinable.

In some examples, light source 132 may be able to generate a signal that may be locked-in with relation to some properties of the signal, the locked-in properties of said signal may be communicated to processor, the processor residing on an electronic device, as described below. In some examples the locked-in signal may be described as a closed loop between light source 134 and coupled electronics, and receiver 134 and coupled electronics.

In some examples, lenses 112 and 114 may be supported in their position via at least two side pieces 116 and 118, where side piece 116 is typically on the right side of gap 110 and side piece 118 is on the left side gap 110. In some examples, focusing lens 112 may be supported by a lens holder 119. In some examples, collimating lens 114 may be supported by lens holder 121, as described below.

A cap 120, or other component configured to cover light source 132, may be typically screwed onto side piece 116 via one or a plurality of screws 141. In some examples, other methods of coupling components together may also be used.

A cap 122, or other component configured to cover receiver 134 may be typically screwed onto side piece 118 via one or a plurality of screws 141. In some examples, other methods of coupling components together may also be used.

In some examples, electronic device 124, typically an integrated circuit, printed circuit board (PCB), printed wiring board (PWB), etched wiring board, printed circuit assembly (PCA), printed circuit board assembly (PCB Assembly or PCBA) may be used to mechanically support and electrically connect electronic components using conductive pathways, tracks or signal traces etched from copper sheets laminated onto a non-conductive substrate within densitometer 100. Typically, electronic device 124 may be coupled to light source 132. In some examples, light source 132 may be physically coupled to electronic device 132.

Light source 132 may send a signal, typically light, through lens 114 through gap 110, any fluid in gap 110, lens 112 to receiver 134.

Electronic device 124 may be configured to interface with a control unit, described below. Electronic device 124 may be configured to be in contact, either wired or wirelessly, with an electronic device coupled to receiver 134.

Electronic device 124 may have electronic connectors; the electronic connects configured to couple electronic device 124 to other components within densitometer 100. In some examples, the electronic contacts may be configured to couple electronic device 124 to other components or devices outside of densitometer 100. Typically, electronic device 124 may be connected to connections to other components in densitometer 100, or components outside densitometer 100 via electronic connectors 210a.

In some examples, electronic device 124 may be configured to be in communication with light source 132. In some examples, electronic device 124 may be configured to control light source 132, such that light source 132 produces a signal, typically light, with predefined characteristics.

In some examples, predefined characteristics may include a known wave function or know wave shape with know frequency and amplitude. In some examples, electronic device 124 may be configured to control light source 132 such that light source 132 produces a signal definable as a sine wave with a predefined frequency of one kilohertz.

Typically electronic device 124 may be in communication with receiver 134. In some examples, electronic device 124 may receive a detected signal from receiver 134. Typically, electronic device 124 may determine the concentration of a fluid by analyzing the detected signal from receiver 134 and comparing detected signal with the generated signal from light source 132.

In some examples, electronic device 124 may be configured to determine the predefined wave of a signal to be a known wave function. Typically, electronic device 124 may be configured to determine the predefined wave of the signal to be a sine wave.

Typically, electronic device 124 may be in communication with receiver 134 such that receiver 134 is configured to specifically filter out a signal not definable by the sine wave with the known frequency produced by light source 132 from other noise in densitometer 100.

In some examples, electronic device 124 may be in communication with receiver 134 such that receiver 134 is configured to specifically filter out a signal not definable by a sine wave with a frequency of one kilohertz, wherein light source 132 produces a signal describable as a sine wave with a frequency of one kilohertz.

In some examples, electronic device 124 may be in communication with receiver 134, such that receiver 134 is configured to detect a signal with a particular sine wave with known frequency and, in some examples, detect changes in amplitude of the signal.

In some examples, electronic device 124 may optimize and/or modulate the frequency of signal from light source 132, such that a ratio of signal to noise is changed.

Receiver 134 may be coupled to electronic device 126. In some examples, receiver 134 may be physically coupled to electronic device 126.

Electronic device 126 may typically be an integrated circuit, printed circuit board (PCB), printed wiring board (PWB), etched wiring board, printed circuit assembly (PCA), printed circuit board assembly (PCB Assembly or PCBA) may be is used to mechanically support and electrically connect electronic components using conductive pathways, tracks or signal traces etched from copper sheets laminated onto a non-conductive substrate within densitometer 100.

Electronic device 126 may have electronic connectors; the electronic connectors 210*b* configured to couple electronic device 126 to other components within densitometer 100. In some examples, the electronic contacts may be configured to couple electronic device 126 to other components or devices outside of densitometer 100. Typically, electronic device 124 may be connected to connections to other components in densitometer 100, or components outside densitometer 100 via electronic connectors 210*b*.

In some examples, there may be kinematic coupling between electronic device 124 and a light source holder 128. In some examples, there may be kinematic coupling between electronic device 124 and side piece 116.

In some examples, there may be kinematic coupling between electronic device 126 and a receiver holder 130. In some examples, there may be kinematic coupling between electronic device 126 and side piece 118.

Typically, kinematic coupling may involve a kinematic tooth, as described below on one component, in some examples, the one component may be side piece 116 and/or side piece 118. The kinematic tooth may be inserted into a kinematic slot, as described below in a second component. In some examples, the second component may be electronic device 124 or electronic device 126, or other components of densitometer 100. In some examples, kinematic slot may be in electronic device 124 and/or electronic device 126.

In some examples, there may be one or a plurality of waterproofing connections 136, e.g., gaskets, o-rings, or other connectors, configured to waterproof densitometer 100, such that densitometer may be immersed fully or partially in a liquid, e.g., ink.

Typically, densitometer includes a spacer piece 140. In some examples, spacer piece may be shaped like a capital "I". Spacer piece 140 may be coupled via kinematic coupling to side piece 116 and side piece 118. Typically, kinematic coupling may involve a kinematic tooth, as described below, on one component, in some examples, on side piece 116 and/or side piece 118, inserted into a kinematic slot in a second component. In some examples, kinematic slot may be in spacer piece 140. In some examples, kinematic slot may be in another component within densitometer 100.

Typically, kinematic coupling slots and teeth, described above and below, may fix some or all 6 degrees of freedom. Typically, these degrees of freedom include three translational degrees of freedom: x, y and z and three rotation, and yaw, pitch and roll. Typically, the 6 degrees of freedom may be fixed along the mating planes of the components, the mating planes as described below, coupled via kinematic coupling in densitometer 100.

Figure 2:
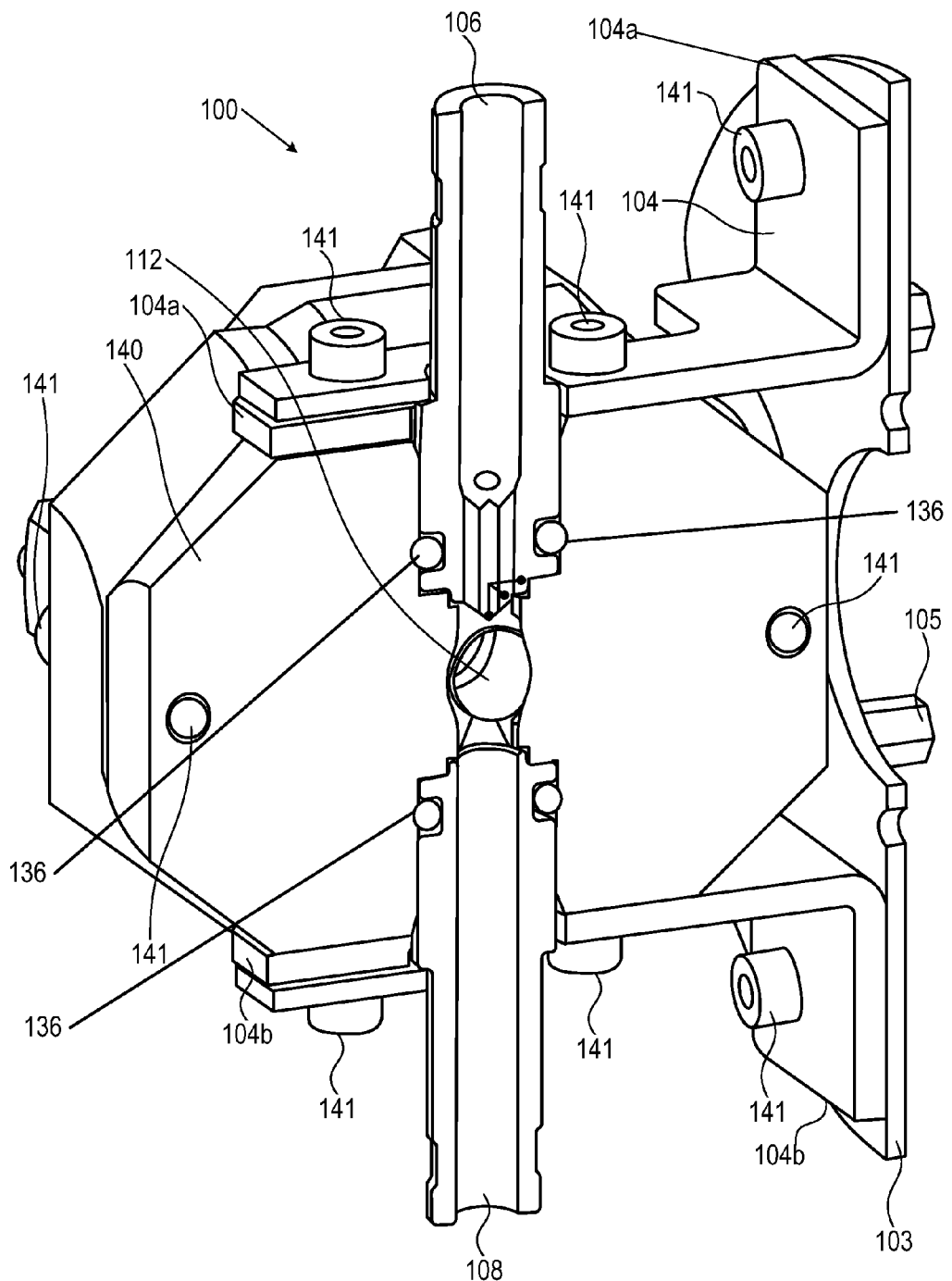
FIG. 2 is a schematic diagram of cross section along a lateral plane of a densitometer, according to an example.

FIG. 2 is a schematic diagram of cross section between along a lateral plane of a densitometer, between a left side and a right side of a densitometer and through the center line of the densitometer, with some of a spacer piece, and a side piece, cut away.

Typically, densitometer 100 components may be coupled together at one or a plurality of connection points, typically, via one or a plurality of screws 141, the screws typically fitting into screw sockets. In some examples, other methods of coupling components together may also be used.

The cross section depicted in the figure provides a view of the spacer piece 140 surrounding inlet 106, outlet 108 and gap 110, between lens 112 and lens 114. Parts of lens 112 may not be shown in this illustration.

As described above, support plate 103 is coupled a base plate via spacer support columns 105. In some examples, other methods of coupling support plate 103 to a base plate may also be used.

As described above, support structure 104 may be typically coupled to support plate 103. Support structure 104*a* typically may be coupled to an upper portion of densitometer 100, near an inlet 106. Typically, this coupling may be via screws 141. In some examples, other methods of coupling components together may also be used.

Support structure 104*b* may be coupled to a lower portion of densitometer 100, near an outlet 108. Typically, this coupling may be via screws 141. In some examples, other methods of coupling components together may also be used.

As described above, in some examples, there may be one or a plurality of waterproofing connections 136, e.g., gaskets, o-rings, or other connectors, configured to waterproof densitometer 100, such that densitometer may be immersed fully or partially in a liquid, e.g., ink, as described above.

Typically, spacer piece 140 is constructed and/or machined from a solid piece of material. In some examples, the material is steel. In some examples, the material may be an alloy. In some examples, other materials may be used.

Figure 3:
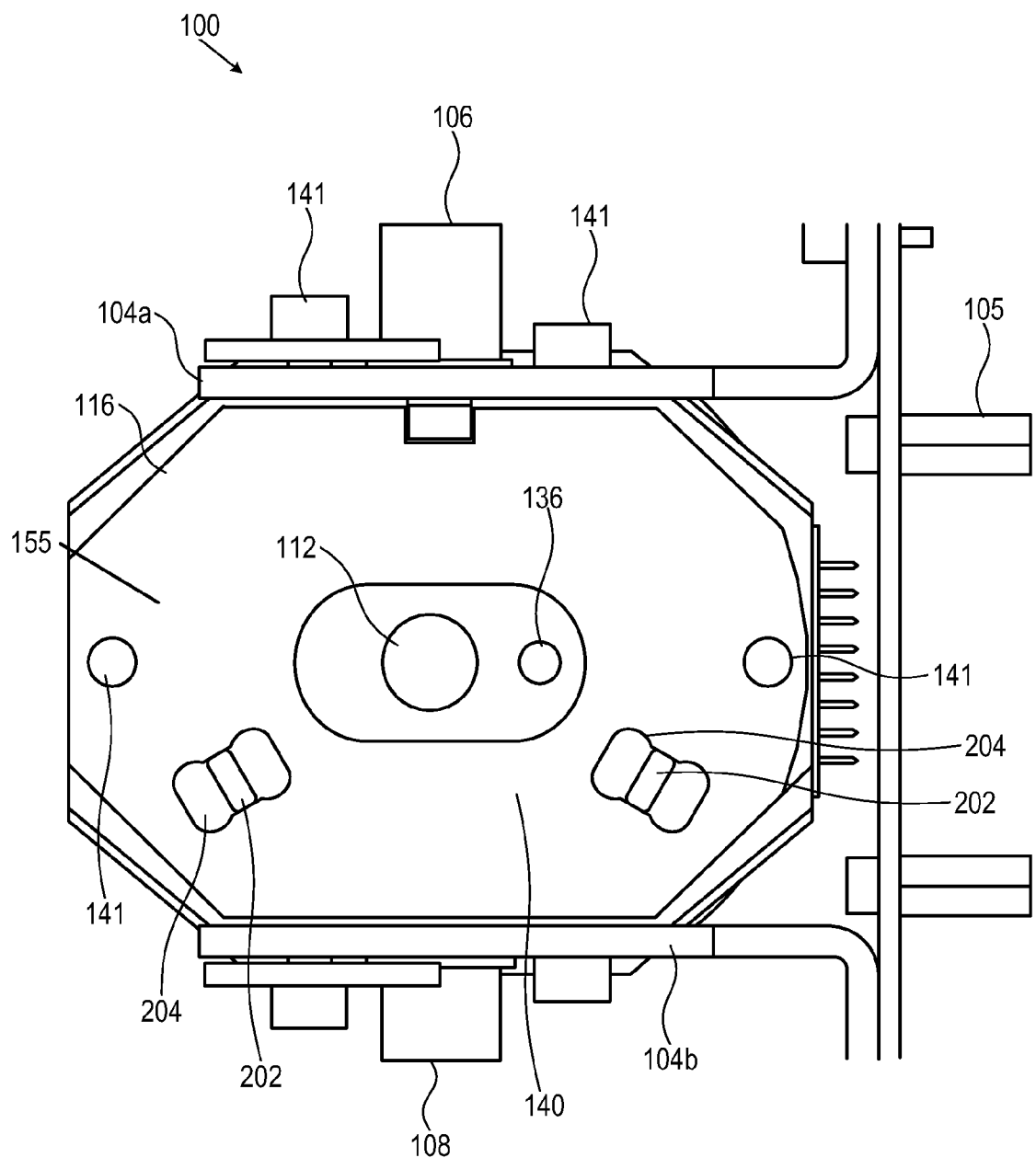
FIG. 3 is a schematic diagram of close-up of an off-center cross section, along a lateral plane of a densitometer, according to an example; and, FIG. 4 is a schematic illustration depicting some connections with a control unit.

FIG. 3 is a schematic diagram of close up of an off-center cross section along a lateral plane of a densitometer, between a left side and a right side of a densitometer. The illustration depicts a mating plane where a spacer piece and a side piece are coupled.

As described above, typically, densitometer 100 components may be coupled together at one or a plurality of connection points, typically, via one or a plurality of screws 141. In some examples, other methods of coupling components together may also be used.

As described above support plate 103 is coupled a base plate via spacer support columns 105. In some examples, other methods of coupling support plate 103 to a base plate may also be used.

As described above, support structure 104 may be typically coupled to support plate 103. Support structure 104a typically may be coupled to an upper portion of densitometer 100, near an inlet 106. Typically, this coupling may be via screws 141. In some examples, other methods of coupling components together may also be used.

Support structure 104b may be coupled to a lower portion of densitometer 100, near an outlet 108. Typically, this coupling may be via screws 141. In some examples, other methods of coupling components together may also be used.

Typically, this coupling may be via screws 141. In some examples, other methods of coupling components together may also be used.

As described elsewhere, in some examples, there may be one or a plurality of waterproofing connections 136, e.g., gaskets, o-rings, or other connectors, configured to waterproof densitometer 100, such that densitometer may be immersed fully or partially in a liquid, e.g., ink, as described above.

The cross section depicted in the figure provides a view of the spacer piece 140 surrounding inlet 106, outlet 108 and gap 110, between lens 112 and lens 114. Parts of lens 112 may not be shown in this illustration, as described above.

Components of densitometer 100 are further coupled together via kinematic or quasi kinematic coupling.

Typically, one component of densitometer 100 may have a slot 204, the slot configured to fix one or a plurality of degrees of freedom along a mating planes of two or more components, one mating plane 155 is show here illustratively, the illustrative mating plane combining both the slot 204 and the tooth 202 from the mating planes: The figure shows at least three teeth 202 illustratively. Typically, teeth 202 are part of side pieces 116 and 118 and mate with slots 204. Typically, spacer piece 140 may have slots 204 that mate with teeth 202 on side pieces 116 and 118. In some examples, spacer piece may have teeth 202 that mate with slots 204 on side pieces 116 and on side piece 118.

Typically, slot 204 may be configured to fix one or a plurality of degrees of freedom along mating planes of two or more components via engaging a tooth 202. Typically, in quasi kinematic coupling, tooth 202 may be short and/or straight. In some examples, tooth 202 may have a very small clearance with slot 204. Typically, this smaller clearance may replace point contact, and in some examples, may enable the use of a softer material in the surfaces of densitometer 100 in general, and at the points of contacts, in particular.

In some examples, slots 204 may have precise dimensions in one axis, e.g., longitudinally, and may have relief dimensions in a second axis, e.g., laterally.

In some examples, slots 204 may have relief dimensions in one axis, e.g., longitudinally, and may have precise dimensions in a second axis, e.g., laterally.

In some examples, some components of densitometer 100 may have slots 204 for coupling to side pieces 118 and 116 and may also have slots 204 for coupling to other and/or additional components of densitometer 100.

In some examples, electronic device 124 of densitometer 100 may have slots 204 for coupling to side piece 116 and may also have slots 204 for coupling to light source 132.

In some examples, some slots 204 in electronic device 124, may be configured for coupling to side piece 116, and may form the geometry of a larger triangle. In some examples, some slots 204 in electronic device 124, may be configured for coupling to light source 132, and may form the geometry of a smaller triangle.

In some examples, electronic device 126 of densitometer 100 may have slots 204 for coupling to side piece 118 and may also have slots 204 for coupling to receiver 134.

In some examples, some slots 204 in electronic device 126, may be configured for coupling to side piece 118, and may form the geometry of a larger triangle. In some examples, some slots 204 in electronic device 126, may be configured for coupling to receiver 134, and may form the geometry of a smaller triangle.

Typically, spacer piece 140 may have one or a plurality of slots on a mating plane 155, the slots typically located in positions wherein they provide a triangular shape, the triangular shape creating a coupling centroid within a coupling triangle, in some examples, deterministically constraining some, in some examples, some or all six degrees of freedom of motion.

Typically, this triangular geometry provides a particular set of contact forces, contact stresses, and contact deflections. The coupling geometry may also typically provide improved precision with reasonable stiffness. The coupling geometry may also provide a weakly over-constrained interaction between the components, but allowing for sub-micron repeatability, a sealing contact, and high stiffness.

Typically, the coupling triangle geometry of this figure may be defined by lines which connect the coupling joints (e.g., tooth 202 and slot 204) coordinate systems. The coupling centroid may be defined as the intersection of the angle bisectors of the included angles of the coupling triangle.

Typically, the quasi kinematic coupling shown in the figure with the triangle geometry provides for easy assembly: if the coupling joints do not form an equilateral triangle, the coupling may typically be limited to be assembled in one configuration.

Typically, in a kinematic or quasi-kinematic coupling, the particular choice of coupling joint location has a strong influence on the rotational stiffness of the coupling. Typically, the device may be constructed such that the coupling joints are located to define the widest possible triangle, subject to geometry/size constraints of the design.

In some examples, stability and good overall stiffness may be achieved if slots 204 are oriented such that the normals to the planes containing the contact forces bisect the angles of the coupling triangle.

In some examples, coupling joints may be aligned to provide maximum resistance to error causing loads in one direction, while providing reasonable stiffness in the perpendicular direction.

Typically, to provide resistance to motion due to the friction induced torques between the screws 141, support plate 103, and base plate 102, the coupling joints are positioned such that they form as large a triangle as possible.

Figure 4:
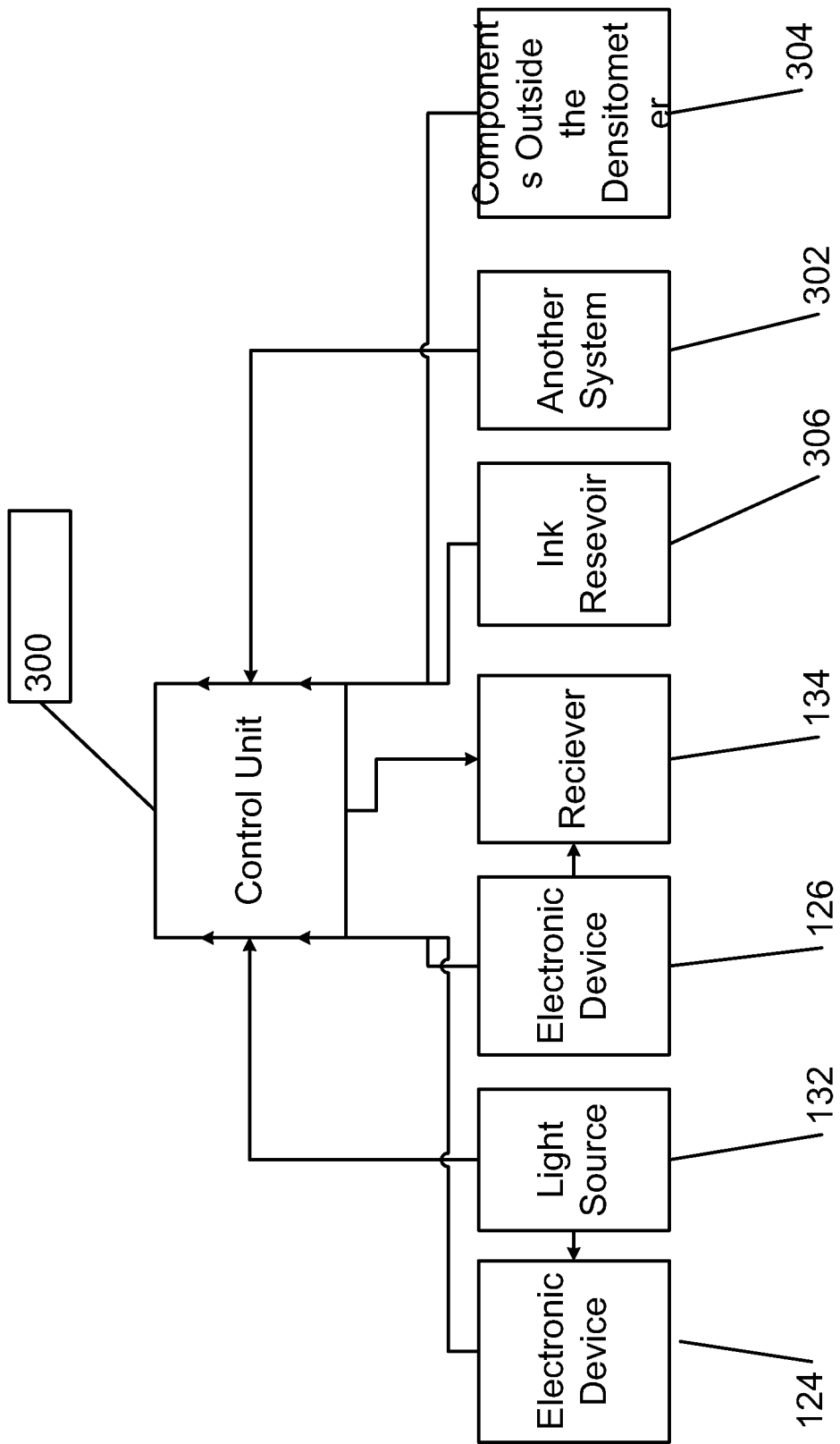

FIG. 4 is a schematic illustration of some of the interactions of a control unit 300. For example, a control unit 300 may be configured to determine, based on data regarding the traveling of light from light source 132 across gap 110, an experimental optical density of a fluid, the fluid passing from inlet 106 through gap 110 through outlet 108.

In some examples, control unit 300 may be configured to determine, based on data regarding the traveling of light from light source 132 across gap 110, an experimental optical density of ink, the ink passing from inlet 106 through gap 110 through outlet 108.

In some examples, control unit 300 may compare this experimental or observed optical density with a predicted optical density, and alter the fluid accordingly, as described below.

In some examples, control unit 300 may compare an experimental or observed optical density of an ink with a predicted optical density of the ink and alter the ink accordingly, as described below.

In some examples, control unit 300 may also control or be in contact with other components of densitometer 100, including electronic device 124. In some examples, control unit may be in contact with electronic device 126.

In some examples, control unit 300 may also control or be in contact with other components of densitometer 100, including light source 132 and receiver 134.

In some examples, control unit 300 may also control or be in contact with components outside the densitometer 304.

Control unit 300, in some examples, may control the flow of liquid from inlet 106 to outlet 108. In some examples, control unit 300 may control the flow of liquid via control over ink reservoir 306.

Control unit 300 may extract data from receiver 134 from a sampled duration, e.g., sample data from densitometer 100 over a number instances of fluid flowing through gap 110, or time, in order to increase the accuracy of measurements of the optical density of fluid.

In some examples, in response to the assessed optical density of fluid, as measured by densitometer 100, control unit 300 may signal another system 302 to alter the makeup of the fluid, such that the experimental optical density of the fluid is changed to reflect the expected optical density. In some examples, control unit may signal another system in a printer apparatus to alter the makeup of ink such that the experimental optical density of the ink is changed.

What is claimed is:

1. An optical measuring device comprising:
    a plurality of components consecutively arranged, coupled together via quasi kinematic or kinematic coupling, and defining a void within, the void enclosing a measuring set-up for measuring at least one optical characteristic of a fluid passing through a gap, the gap located at an intersection between an optical path of the measuring set-up and a flow path of the fluid,
    the measuring set-up including a light source, at least one lens, and a light receiver,
    the plurality of components comprising a first component surrounding the gap, a second component supporting the at least one lens, and an electronic device connected to at least one of the light source and the light receiver.

2. The device of claim 1, wherein the at least one lens of the measuring set-up comprises a focusing lens and a collimating lens.

3. The device of claim 1, further comprising a fluid inlet and a fluid outlet, wherein the flow path is from the fluid inlet to the fluid outlet.

4. The device of claim 1, wherein the quasi kinematic or kinematic coupling includes a coupling of one or a plurality of teeth with one or a plurality of slots along a mating plane.

5. The device of claim 1, wherein the optical measuring device comprises a densitometer, the densitometer configured to measure an optical density of an ink passing from an ink reservoir to a printer head.

6. The device of claim 1, wherein the first component is quasi kinematically or kinematically coupled to the second component, and wherein the electronic device is quasi kinematically or kinematically coupled to the second component.

7. The device of claim 6, wherein the quasi kinematic or kinematic coupling of the first component to the second component and of the electronic device to the second components include a coupling of teeth with slots.

8. The device of claim 6, further comprising a fluid inlet and a fluid outlet, the flow path extending from the fluid inlet to the fluid outlet, and wherein the first component further surrounds at least portions of the fluid inlet and fluid outlet.

9. The device of claim 1, wherein the flow path is generally perpendicular to the optical path that extends from the light source through the at least one lens to the light receiver.

10. A method of constructing an optical measuring device for use in measuring an optical characteristic of a fluid, comprising:
    coupling a plurality of components, consecutively arranged, via quasi kinematic or kinematic coupling, the coupling of the components defining a void within, the void enclosing a measuring set-up for measuring at least one optical characteristic of the fluid passing through a gap, the gap located at an intersection between an optical path of the measuring set-up and a flow path of the fluid,
    the measuring set-up including a light source, at least one lens, and a light receiver,
    the plurality of components comprising a first component surrounding the gap, a second component supporting the at least one lens, and an electronic device connected to at least one of the light source and the light receiver.

11. The method of claim 10, wherein the first component comprises a spacer, the second component comprises a first side piece, and the plurality of components further comprise a second side piece, the at least one lens of the measuring set-up including a first lens and a second lens, the first side piece supporting the first lens, and the second side piece supporting the second lens.

12. The method of claim 10, wherein the quasi kinematic or kinematic coupling includes a coupling of one or a plurality of teeth with one or a plurality of slots along a mating plane.

13. The method of claim 10, wherein the first component is quasi kinematically or kinematically coupled to the second component, and the electronic device is quasi kinematically or kinematically coupled to the second component.

14. The method of claim 10, wherein the flow path is generally perpendicular to the optical path that extends from the light source through the at least one lens to the light receiver.

15. A system comprising:
    a printer; and
    an optical measuring device comprising:
        a plurality of components consecutively arranged, coupled together via quasi kinematic or kinematic coupling, and defining a void within, the void enclosing a measuring set-up for measuring at least one optical characteristic of an ink of the printer passing through a gap, the gap located at an intersection between an optical path of the measuring set-up and a flow path of the ink,
        the measuring set-up including a light source, at least one lens, and a light receiver,
        the plurality of components comprising a first component surrounding the gap, a second component supporting the at least one lens, and an electronic device connected to at least one of the light source and the light receiver.

16. The system of claim 15, wherein the at least one lens of the measuring set-up comprises a focusing lens and a collimating lens.

17. The system of claim 15, wherein the quasi kinematic or kinematic coupling includes a coupling of one or a plurality of teeth with one or a plurality of slots along a mating plane.

18. The system of claim 15, wherein the flow path is generally perpendicular to the optical path that extends from the light source through the at least one lens to the light receiver.

* * * * *